United States Patent [19]

Chen

[11] Patent Number: 5,262,468

[45] Date of Patent: * Nov. 16, 1993

[54] THERMOPLASTIC ELASTOMER GELATINOUS COMPOSITIONS

[75] Inventor: John Y. Chen, Pacifica, Calif.

[73] Assignee: Applied Elastomerics, Inc., Pacifica, Calif.

[*] Notice: The portion of the term of this patent subsequent to Jan. 18, 2000 has been disclaimed.

[21] Appl. No.: 705,711

[22] Filed: May 23, 1991

Related U.S. Application Data

[63] Continuation-in-part of Ser. No. 211,426, Jun. 24, 1988, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^5$ ................................ C08K 5/01
[52] U.S. Cl. ............................ 524/476; 524/490; 524/505; 525/95
[58] Field of Search ............... 524/505, 476, 490; 525/95

[56] References Cited

U.S. PATENT DOCUMENTS

| | | |
|---|---|---|
| 3,485,787 | 12/1969 | Haefele . |
| 3,676,387 | 7/1972 | Lindlof . |
| 3,827,999 | 8/1974 | Crossland ............ 260/33.6 |
| 4,151,057 | 4/1979 | St. Clair . |
| 4,176,740 | 11/1979 | Sabia ............ 174/23 |
| 4,259,540 | 3/1981 | Sabia ............ 174/23 |
| 4,351,913 | 9/1982 | Naren ............ 523/218 |
| 4,369,284 | 1/1983 | Chen . |
| 4,432,607 | 2/1984 | Levy . |
| 4,492,428 | 1/1985 | Levy ............ 350/96.30 |
| 4,497,538 | 2/1985 | Patel . |
| 4,509,821 | 4/1985 | Stenger . |
| 4,600,261 | 7/1986 | Debbaut . |
| 4,618,213 | 10/1986 | Chen . |
| 4,680,233 | 7/1987 | Camin . |
| 4,709,982 | 12/1987 | Corne ............ 350/96.23 |
| 4,716,183 | 12/1987 | Gamarra . |
| 4,822,834 | 4/1989 | Blevins . |
| 4,833,193 | 5/1989 | Sieverding ............ 524/486 |
| 4,865,905 | 9/1989 | Uken ............ 428/220 |
| 4,900,877 | 2/1990 | Drbrow ............ 174/35 |
| 4,942,270 | 7/1990 | Gamarra ............ 174/93 |

FOREIGN PATENT DOCUMENTS 1268431 1/1969 United Kingdom .

OTHER PUBLICATIONS

SC:1102-89 (4-89) "Kraton Thermoplastic Rubbers in Oil Gels" Shell.

*Primary Examiner*—Herbert J. Lilling

[57] ABSTRACT

A novel gelatinous composition is disclosed which contains an intimate melt blend admixture of poly(styrene-ethylene-butylene-styrene) triblock copolymer and high levels of a plasticizing oil.

The gelatinous composition is transparent and have a novel combination of properties including unexpectedly high elongation and tensile strength and excellent shape retention after extreme deformation under high-velocity impact and stress conditions. The gelatinous products of this invention are soft, flexible, and have elastic memory, characterized by a gel rigidity of from about 20 gram to about 700 gram Bloom. These and other properties are particularly essential for the gelatinous composition to have utility as toys, therapeutic hand exercising grips, shock absorbers, acoustical isolators, and other uses.

6 Claims, 1 Drawing Sheet

THERMOPLASTIC ELASTOMER GELATINOUS COMPOSITIONS

REFERENCE TO RELATED APPLICATIONS AND PATENTS

This application is a continuation-in-part of copending application Ser. No. 211,426 filed Jun. 24, 1988 which is a continuation-in-part application Ser. No. 921,752 filed Oct. 21, 1986 which is a continuation-in-part of application Ser. No. 572,172, filed Jan. 18, 1984 and issued as Pat. No. 4,618,213 on Oct. 21, 1986, which is a continuation-in-part of application Ser. No. 458,703, filed Jan. 17, 1983, which is a continuation-in-part of application Ser. No. 134,977, filed Mar. 28, 1980 and issued as Pat. No. 4,369,284 on Jan. 18, 1983, which in turn is a continuation-in-part of application Ser. No. 916,731, filed Jun. 19, 1978, now abandoned which is a continuation-in-part of application Ser. No. 815,315, filed Jul. 13, 1977, now abandoned which is a continuation-in-part of application Ser. No. 778,343, filed Mar. 17, 1977 now abandoned. The subject matter contained in the related applications and patents are specifically incorporated herein by reference.

FIELD OF THE INVENTION

The present invention relates to a thermoplastic elastomer gelatinous composition and useful articles made therefrom.

BACKGROUND OF THE INVENTION

It is well known that thermoplastic elastomers, more particularly, thermoplastic block copolymers can be oil-extended to produce soft and flexible compositions. The oil plasticized thermoplastic block copolymer compositions of the prior art, however, suffers from one or more poor physical and mechanical properties such as poor breaking strength, poor elongation, poor craze, tear, creep, and crack resistance, and poor oil acceptance, to name a few. For instance, Shell Technical Bulletin No. SC 65-75 teaches the use of low viscosity poly(styrene-ethylene-butylene-styrene) triblock copolymers (Kraton G 1650 and G 1652) having styrene end block to ethylene and butylene center block ratio of 28:72 and 29:71 and with Brookfield Viscosities of 1,500 and 550 cps (viscosity being measured for a solution of 20 weight percent solids in toluene at 25° C.) respectively in blends with butyl rubber, tackifier, filler, and oil. In none of the blends, however, are the properties of the compositions desirable; but rather, the use of other polymers such as butyl rubber, tackifiers, and fillers for extending and plasticizing the triblock copolymers result in dimensionally unstable mastic like materials which are not acceptable for purposes of the present invention. Furthermore, when the low viscosity triblock copolymers as disclosed in Shell's Bulletin No. SC 65-75 are plasticized with oil, the compositions obtained show decreases in the desired properties such as poor elongation and tensile strength, poor creep, craze, tear, and crack resistance; in addition, these compositions of the prior art trend to rupture and crumble when submitted to moderate shearing stress conditions.

SUMMARY OF THE INVENTION

Accordingly, it is an object of the present invention to provide compositions substantially free of one or more of the disadvantages of prior art compositions.

Another object is to provide gelatinous elastomer compositions which are transparent.

Yet another object is to provide gelatinous elastomer compositions of high dimensional stability, excellent crack, tear, craze, and creep resistance, improved tensile strength and high elongation.

A still further object is to provide gelatinous elastomer compositions having long service life under vibrational stress, and allows for repeated handling.

Another object is to provide gelatinous elastomer compositions having excellent processing ability for cast moulding.

Yet another object is to produce transparent, dimensionally stable, non-toxic, nearly tasteless and odorless, extremely soft, highly flexible, and easily hand deformable moulded gelatinous elastomer articles possessing elastic memory from compositions of the instant invention.

Another object is to provide transparent gelatinous elastomeric optical lenses and light conducting articles such as rods, tubes, and the like which are extremely soft, highly flexible, easily hand deformable, posses elastic memory, and other desired properties.

Still another object is to provide gelatinous elastomeric articles which are washable and useful for removing lint and other particulate matter.

Another object is to provide gelatinous elastomeric articles useful for noise and vibration control, for medical and sport health care, for novel amusement toys, for high vacuum sealing incorporating a mineral oil-based magnetic fluid and the like.

Other objects, aspects and advantages of the invention will become apparent to those skilled in the art upon consideration of the accompanying disclosure.

In accordance with the present invention, I have unexpectedly discovered that a gelatinous elastomer composition having novel combination of properties can be provided by melt blending an admixture consisting essentially of:

(A) 100 parts by weight of a high viscosity triblock copolymer of the general configuration poly(styrene-ethylene-butylene-styrene) where said triblock copolymer is characterized as having a Brookfield Viscosity of a 20 weight percent solids solution of said triblock copolymer in toluene at 25° C. of at least about 1,800 cps.

(B) from about 300 to about 1,600 parts by weight of an plasticizing oil.

The high viscosity triblock copolymers in (A) which are suitable for use in the present invention has a typical Brookfield Viscosity of a 20 weight percent solids solution in toluene at 25° C. of not less than about 1,800 cps, and preferably about 2,000 cps or higher. Typically, the Brookfield Viscosity values of (A) can range from about 1,800 cps to about 16,000 cps. Less typically, the Brookfield Viscosity values of (A) can range from about 1,800 cps to about 30,000 cps or higher.

The proportion of hydrocarbon plasticizing oil in (B) is more preferably from about 350 to about 1,600 parts per 100 parts of the triblock copolymer.

The various aspects and advantages of the invention will become apparent to those skilled in the art upon consideration of the accompanying disclosure and the drawings.

DESCRIPTION OF THE PREFERRED EMBODIMENTS

Figure 1:
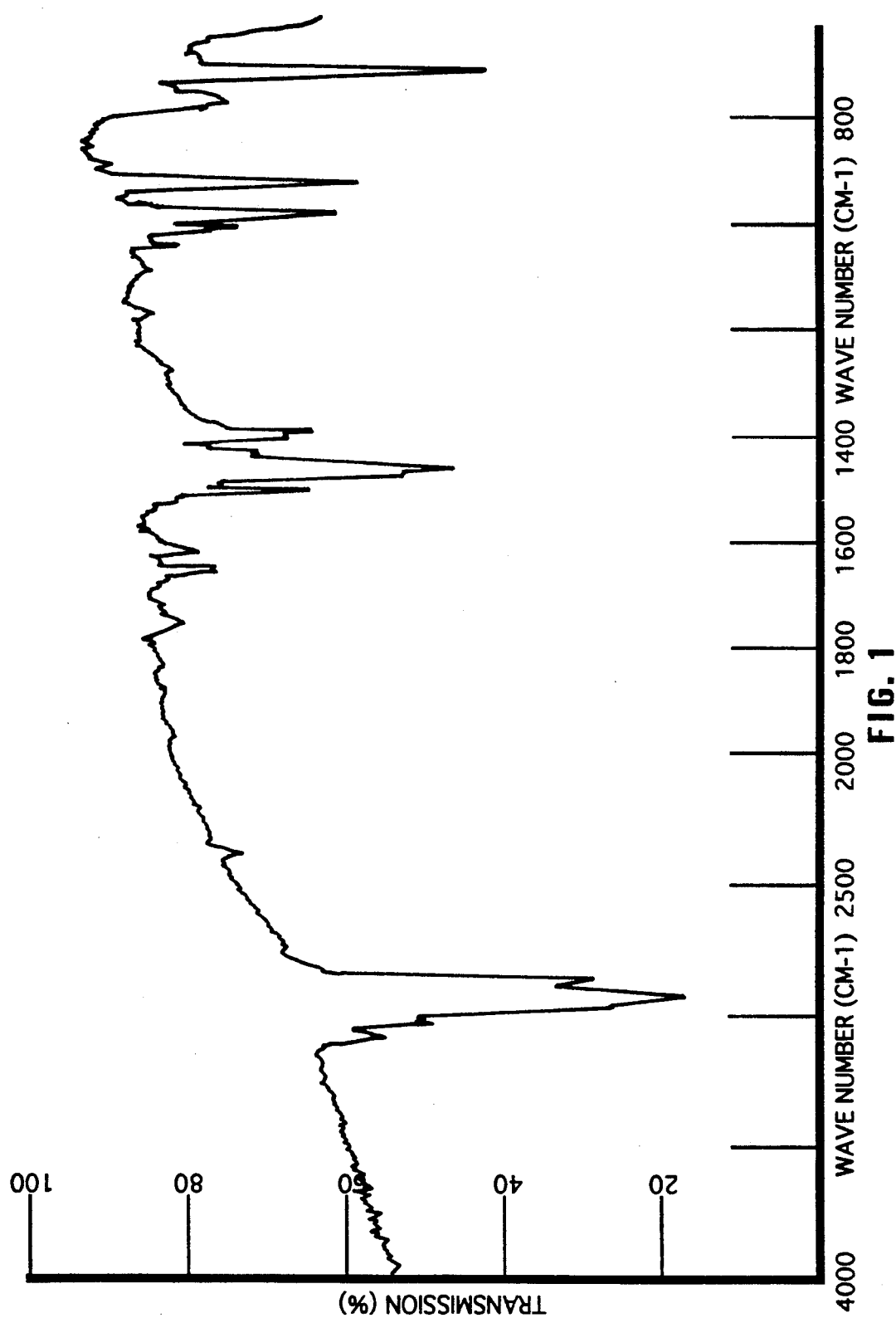
FIG. 1. An IR spectrum trace of a SEBS triblock copolymer.

The high viscosity triblock copolymers employed in the present invention have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "ENCYCLOPEDIA OF POLYMER SCIENCE AND ENGINEERING", Volume 2 and 5, 1987-1988; "Thermoplastic Elastomers", MODERN PLASTIC ENCYCLOPEDIA, 1989; and Walker, B. M., Ed,. et al., HANDBOOK OF THERMOPLASTIC ELASTOMERS, Van Nostrand Reinhold Co., 2nd Edition, 1988. There publications are incorporated herein by reference).

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C. An IR spectrum trace of Kraton G 1855X is shown in FIG. 1.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, these ratios can vary broadly from the typical product specification values. For example, the styrene to ethylene and butylene weight ratio for Kraton G 1651, G4600, G 4609, and G 1855X can range from lower than about 20:80 to above about 40:60. More specifically, Kraton G 1651, Kraton G 1855X, Kraton G 4600, Kraton G 4609 Kraton G 1855X can have varying ratio values including 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 52:49 and the like. Other ratio values of less than 19:81 or higher than 52:49 are also possible. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers having ratios below 31:69 may be used, but they are less preferred due to their decrease in the desirable properties of the final composition.

Plasticizers particularly preferred for use in practicing the present invention are will known in the art, they include rubber processing oil such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available. Examples of representative commercially oils include Amoco ® polybutenes, hydrogenated polybutenes and polybutenes with epoxide functionality at one end of the polybutene polymer: Example of such polybutenes include: L-14 (320 $M_n$), L-50 (420 $M_n$), L-100 (460 $M_n$), H-15 (560 $M_n$), H-25 (610 $M_n$), H-35 (660 $M_n$), H-50 (750 $M_n$), H-100(920 $M_n$), H-300 (1290 $M_n$), L-14E (27-37 cst @ 100° F. Viscosity), L-300E (635-690 cst @ 210° F. Viscosity), Actipol E6 (365 $M_n$), E16 (973 $M_n$), E23 (1433 $M_n$) and the like. Examples of various commercially oils include: ARCO Prime and Tufflo oils, other white mineral oils include: Bayol, Bernol, American, Blandol, Drakeol, Ervol, Gloria, Kaydol, Litetek, Marcol, Parol, Peneteck, Primol, Protol, Sontex, and the like.

The high viscosity triblock copolymer component by itself lacks the desired properties; whereas, when the triblock copolymer (having Brookfield Viscosities of a 20 weight percent solids solution in toluene at 25° C. of about 1,800 cps or higher and styrene to ethylene and butylene ratio preferably of the range contemplated in the instant invention) is combined with selected plasticizing oils with an average molecular weight preferably of about 200 to about 700, as determined by ebulliscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity preferably of about 20 gram or lower to about 700 gram Bloom and substantially without oil bleedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

In accordance with the practice of the present invention, the aforementioned molecular weight range plasticizing oils are most preferred. Generally, plasticizing oils with average molecular weights less than about 200 and greater than about 700 may also be used.

The composition of this invention can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

Additives useful in the composition of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearylpentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl]-benzene), 4,4"-methylenebis(2,6-di-tert-butylphenol), steraric acid, oleic acid, stearamide, behenamide, oleamide, erucamide, N,N"'-ethylenebisstearamide, N,N"-ethylenebisoleamide, sterryl erucamide, erucyl erucamide, oleyl palmitamide, stearyl stearamide, erucyl stearamide, metallic pigments (aluminum and brass flakes), $TiO_2$, mica, fluorescent dyes and pigments, phosphorescent pigments, aluminatrihydrate, antimony oxide, iron oxides ($Fe_3O_4$-$Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on *Magnetic Materials*, Publication NMAB-426, National Academy Press (1985) is incorporated herein by reference.

The gelatinous elastomer compositions of the present invention are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amount of SEBS used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The instant composition is excellent for cast moulding and the moulded products have various excellent characteristics which cannot be anticipated form the properties of the raw components. Other conventional methods of forming the composition can be utilized.

The basis of this invention resides in the fact that a high viscosity poly(styrene-ethylene-butylene-styrene) triblock copolymer having styrene end block to ethylene and butylene center block ratio preferably within the contemplated range of from about 20:80 to about 40:60, more preferably from between about 31:69 to about 40:60 when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/cm², low elongation set at break of substantially not greater than about 2%, tear resistance of at least $5 \times 10^5$ dyne/cm², substantially about 100% snap back when extended to 1,200% elongation, and a gel rigidity of substantially not greater than about 700 gram Bloom. It should be noted that when the ratio falls below 31:69, various properties such as elongation, tensile strength, tear resistance and the like can decrease while retaining other desired properties, such as gel rigidity, flexibility, elastic memory.

More specifically, the gelatinous composition of the present invention exhibit one or more of the following properties. These are: (1) tensile strength of about $8 \times 10^5$ dyne/cm² to about $10^7$ dyne/cm²; (2) elongation of about 1,600% to about 3,000% and higher; (3) elasticity modulus of about $10^4$ dyne/cm² to about $10^6$ dyne/cm²; (4) shear modulus of about $10^4$ dyne/cm² to about $10^6$ dyne/cm² as measured with a 1, 2, and 3 kilogram load at 23° C.; (5) gel rigidity of about 20 gram Bloom or lower to about 700 gram Bloom as measured by the gram weight required to depress a gel a distance of 4 mm with a piston having a cross-sectional area of 1 square cm at 23° C.; (6) tear propagation resistance of at least about $5 \times 10^5$ dyne/cm²; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gelatinous elastomer articles moulded from the instant compositions have various additional important advantages in that they do not crack, creep, tear, crack, or rupture in flextural, tension, compression, or other deforming conditions of normal use; but rather the moulded articles made from the instant composition possess the intrinsic properties of elastic memory enabling the articles to recover and retain its original moulded shape after many extreme deformation cycles as compared to prior art triblock copolymer oil-extended compositions. In applications where low rigidity, high elongation, good compression set and excellent tensile strength are important, the instant compositions would be preferred.

The gelatinous elastomer compositions of the present invention are useful in low frequency vibration applications, such as viscoelastic layers in constrained-layer damping of mechanical structures and goods, as viscoelastic layers used in laminates for isolation of acoustical and mechanical noise, as antivibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The components are also useful as moulded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. The compositions are also useful for forming various shaped articles for use as novel amusement toys. The compositions of the invention are useful as novel reusable lint removers for cleaning the computer mouse, computer and typewriter keyboards, camera lenses, LP records, various hard-to-clean corners of a car interior, and other nooks and crannies on the surface or inside buildings, houses, schools, ships, offices, and etc. The composition can also be formed into shapes for use as optical lenses, as light conductors in the form of pipes, tubes, cylinders, rods, prisms, cones, spheres and the like. The optical lenses may have two or more opposite regular surfaces either both curved or one curved and the other plane. Such lenses may be used either singly or combined in an optical instrument or in the hand for forming an image by focusing rays of light. Example of lens shapes include plano-convex, bi-convex, converging meniscus, plano-concave, bi-concave, diverging meniscous, cylindrical, and spherical. Other uses may include as cladding for cushioning optical fibers from bending stresses, as fishing bate, as a high vacuum seal (against atmosphere pressure) which contains a useful amount of a mineral oil-based magnetic fluid particles, etc.

As an example of the versatility of use of the instant composition, a hand exerciser can be made in any shape so long as it is suitable for use as a hand exerciser: a sphere shape, a cube shape, a rectangular shape, etc. Likewise, a wheelchair cushion can be made from the composition in almost any shape so long as it meets the needs of the user of the cushion. The same applies for brace cushions for the hand, wrist, finger, forearm, knee, leg, etc.

Another versatile usefulness of the composition is dental flossing. The dental floss can be almost any shape so long as it is suitable for flossing. A thick shaped piece of the composition can be stretched into a thin shape and used for flossing. A thinner shaped piece would require less stretching, etc.

Another example, the composition can be formed into any shape and used as a lint remover. A article of a suitable shape and size can be used as a lint remover just by contacting the article onto any surface containing lint; the lint is left-off by the composition regardless of its shape. Another use of the composition is forming the tips of swabs.

The instant compositions can be formed in any shape; the original shape can be deformed into another shape (to contact a regular or irregular surface) by pressure and upon removal of the applied pressure, the composition in the deformed shape will recover back to its original shape.

The compositions of the invention can be casted unto various substrates, such as open cell materials, metals, ceramics, glasses, plastics, etc. Useful open-cell plastics include: polyamides, polyimides, polyesters, polyisocyanurates, polyisocyanates, polyurethanes, poly(vinyl alcohol), etc. Open-called Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The invention is further illustrated by means of the following illustrative embodiments, which are given for purpose of illustration only and are not meant to limit the invention to the particular components and amounts disclosed.

EXAMPLE I

A comparison was made between a low viscosity poly(styrene-ethylene-butylene-styrene) triblock copolymer having styrene end block to ethylene and butylene center block ratio below the range between 31:69 to 40:60 and a high viscosity poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties were measured as follows:

Tear Propagation (ASTM D 19938 modified)

6 mm×25 mm×75 mm strips with a 50 mm logitudial razor cut slit were tored through the entire unslited 25 mm portion at a crosshead separation speed of 250 mm per minute.

Cracking (ASTM D 518 Method B modified)

25 mm×50 mm×150 mm long strips were bent 180° until their ends meet making a loop and placed between clamping blocks. The clamping blocks were compressed together under a constant force of 50 gms and the samples were timed from initial application of the 50 gram force until the first appearance of surface cracking resulting in complete failure due to crack growth in the looped portion of the specimen.

Tensile Strength (ATSM D 412 modified)

6 mm×25 mm×100 mm strips were extended at a crosshead separation speed of 508 mm per minute until break.

Ultimate elongation (ASTM D 412 modified)

6 mm×25 mm×100 mm strips were extended at a crosshead separation speed of 508 mm per minute until break.

Tensile Set (ASTM D 412 Modified)

6 mm×25 mm×100 mm strips were mechanically extended at a grip separation speed of 250 mm per minute and maintained at test condition so 50%, 100%, 300%, 400%, 600% and 1,200% elongation for a period of 60 seconds and allowed to freely retract for 10 minutes. The extension remaining after this time period expressed as a % of the original length was recorded as set.

Compression Set (ASTM D 395 modified)

25 mm×25 mm×25 mm cubes were placed in a compression jig with shims under a constant force of 5,000 grams for a periods of 60 seconds, 60 minutes, and 24 hours. The compressive force was removed and set was determined after 30 minutes.

Snap Back 25 mm×25 mm×150 mm strips were hand extended by gripping the ends to elongation settings of 50%, 100%, 200%, 400%, 800%, and 1,200% for 10 seconds and then allowed to snap back. Separate samples were tested at each elongation setting. The measured extension remaining 5 seconds after snap back was used to determine % snap back.

Hand Kneading (60 seconds)

25 mm×25 mm×25 mm cubes were placed in the palm of one hand and kneaded for 60 seconds then examined for appearance and dimensional condition.

TABLE I

| Formulation | S/EB Ratio[1] | Weight Parts | | |
| --- | --- | --- | --- | --- |
| | | A | B | C |
| SEBS[2] | 28:72 | 100 | | |
| SEBS[3] | 29:71 | | 100 | |
| SEBS[4] | 33:67 | | | 100 |
| Paraffinic oil[5] | | 400 | 400 | 400 |
| Stabilizer[6] | | 2.5 | 2.5 | 2.5 |
| Breaking strength[7], dyne/cm$^2$ | | $4 \times 10^5$ | $4 \times 10^5$ | $4 \times 10^6$ |
| Tear propagation[8], dyne/cm$^2$ | | $8 \times 10^4$ | $7 \times 10^4$ | $1 \times 10^6$ |

TABLE I-continued

| Formulation | S/EB Ratio[1] | Weight Parts | | |
|---|---|---|---|---|
| | | A | B | C |
| Compression set[10] at 24 hours | | 81% (R) | 77% (R) | 0.0% |
| Rigidity, gram Bloom | | 1,536 | 1,520 | 360 |

[1]Styrene to ethylene and butylene ratio
[2]Shell Kraton G1650 having a Brookfield viscosity of 1,500 cps as measured for a 20% weight solids solution in toluene at 25° C.
[3]Shell Kraton G 1652 having a Brookfield viscosity of 550 cps as measured for a 20% weight solids solution in toluene at 25° C.
[4]Shell Kraton G 1651 having a Brookfield viscosity of 2,000 cps as measured for a 20% weight solids solution in toluene at 25° C.
[5]ARCO prime 200,
[6]Irganox 1010,
[7]ASTM D 412 modified,
[8]ASTM D 1938 modified,
[9]ASTM D 412 modified,
[10]ASTM D 2395 modified,
(R) ruptured completely The results of Table I show drastically unacceptable poor properties of low viscosity triblock copolymers having styrene to ethylene and butylene ratios which are below the contemplated (less preferred) range of the instant invention.

EXAMPLE II

One hundred parts by weight of a high viscosity poly(styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm². The average gel rigidity values with respect to various oil concentrations are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II was repeated except about 980 parts oil was used and the gel rigidity found to about 101 gram Bloom. Other properties measured were: tensile strength at break about 4.4×10⁶ dyne/cm2, elongation at break about 2,4470%, elasticity modulus about 3.5×10⁴ dyne/cm2, and shear modulus about 3.7×10⁴ dyne/cm2. The tensile strength, elongation, elasticity modulus were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of: 72 parts of a paraffinic oil (ARCO prime 200), 72 pars of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G 4609) having a styrene to ethylene and butylene ratio of about 33:67 was used and the physical properties were found to be about substantially unchanged with respect to the components used in Example I.

EXAMPLE X

Example II was repeated except about 400 parts of oil was used and the properties measured were: tear propagation about 1.4×10⁶ dyne/cm², no crack growth in 180° bend under 50 gram load for 5,000 hours at room temperature, tensile strength about 4×10⁶ dyne/cm2, elongation at break about 1,700%, tensile set about 0% at 1,200% elongation, compression set about 0% when tested under 5,000 gram load for 24 hours, and 100% snap back recovery after extension to 1,200%.

Examples XI-XIV-j below illustrate other modes of practice contemplated.

EXAMPLE XI

The procedure of Example II is repeated except Shell Kraton G 1651, poly(styrene-ethylene-butylene-styrene) triblock copolymer is used having a styrene end block to ethylene and butylene center block ratio of about 32:68 and the gel rigidity is found to be within the range of about 20 to about 700 gram Bloom.

EXAMPLE XII

The procedure of Example II is repeated except Shell Kraton G 1651, poly(styrene-ethylene-butylene-styrene) triblock copolymer, is used having a styrene end block to ethylene and butylene center block ratio of about 34:66 and the gel rigidity is found to be within the range of about 20 to about 700 gram Bloom.

EXAMPLE XIII

The procedure of Example II is repeated except Shell Kraton G 1651, poly(styrene-ethylene-butylene-styrene) triblock copolymer, is used having a styrene end block to ethylene and butylene center block ratio of about 36:64 and the gel rigidity is found to be within the range of about 20 to about 700 gram Bloom.

EXAMPLE XIV

The procedure of Example II is repeated except Shell Kraton G 1651, poly(styrene-ethylene-butylene-styrene) triblock copolymer, is used having a styrene end block to ethylene and butylene center block ratio of about 38:62 and the gel rigidity is found to be within the range of about 20 to about 700 gram Bloom.

EXAMPLE XIV-a

The procedure of Example II is repeated except Shell Kraton G 1651, poly(styrene-ethylene-butylene-styrene) triblock copolymer, is used having a styrene end block to ethylene and butylene center block ratio of about 31:69 and the gel rigidity is found to be within the range of about 10 to about 800 gram Bloom.

EXAMPLE XIV-b

The procedure of Example II is repeated except Shell Kraton G 1651, poly(styrene-ethylene-butylene-styrene) triblock copolymer, is used having a styrene end block to ethylene and butylene center block ratio of about 37:63 and the gel rigidity is found to be within the range of about 10 to about 800 gram Bloom.

EXAMPLE XIV-c

The procedure of Example II is repeated except Shell Kraton G 1651, poly(styrene-ethylene-butylene-styrene) triblock copolymer, is used having a styrene end block to ethylene and butylene center block ratio of about 19:81 and the gel rigidity is found to be within the range of about 10 to about 800 gram Bloom.

EXAMPLE XIV-d

The procedure of Example II is repeated except Shell Kraton G 1651, poly(styrene-ethylene-butylene-styrene) triblock copolymer, is used having a styrene end block to ethylene and butylene center block ratio of about 38:80 and the gel rigidity is found to be within the range of about 10 to about 800 gram Bloom.

EXAMPLE XIV-e

The procedure of Example II is repeated except Shell Kraton G 1651, poly(styrene-ethylene-butylene-styrene) triblock copolymer is used having a styrene end block to ethylene and butylene center block ratio of about 38:62 and the gel rigidity is found to be within the range of about 10 to about 800 gram Bloom.

EXAMPLE XIV-f

The procedure of Example II is repeated except Shell Kraton G 1651, poly(styrene-ethylene-butylene-styrene) triblock copolymer, is used having a styrene end block to ethylene and butylene center block ratio of about 29:71 and the gel rigidity is found to be within the range of about 10 to about 800 gram Bloom.

EXAMPLE XIV-g

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 10 to about 800 gram Bloom.

EXAMPLE XIV-h

The procedure of Example II is repeated except Shell Kraton G 1651, poly(styrene-ethylene-butylene-styrene) triblock copolymer, is used having a styrene end block to ethylene and butylene center block ratio of about 22:78 and the gel rigidity is found to be within the range of about 10 to about 800 gram Bloom.

EXAMPLE XIV-i

The procedure of Example II is repeated except Shell Kraton G 1651, poly(styrene-ethylene-butylene-styrene) triblock copolymer, is used having a styrene end block to ethylene and butylene center block ratio of about 25:75 and the gel rigidity is found to be within the range of about 10 to about 800 gram Bloom.

EXAMPLE XIV-j

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 10 to about 800 gram Bloom.

EXAMPLE XV

A sheet (3 cm×28 cm×43 cm) formed from the composition of Example III was placed in contact with a vertical concrete wall and objects such as ping pong balls, golf balls, and a common clay brick were thrown at it from a distance of about 4 meters. Upon striking the sheet, the various objects adhered to it and were not damaged by the impact.

EXAMPLE XVI

A raw (grade AA large size) hen egg was dropped from a height of about 8 meters on to a sheet (0.5 cm×25 cm×25 cm) formed from the composition of Example III which was expanded to about 5 times the original dimension. Upon striking the expanded sheet, the egg adhered to it and was not damaged.

EXAMPLE XVII

Compositions of Example II are poured into a plano-convex, a bi-convex, a converging meniscus, a plano-concave, a bi-concave, a diverging meniscous, a cylindrical, and a spherical lens forming container. The molten composition was allowed to cool in the containers to room temperature and removed. The resultant lenses are used to image news print and other objects.

EXAMPLE XVIII

Compositions of Example II are continuously extruded into 1 meter length rod shape articles through a 0.05, a 0.1, a 0.2, a 0.4, a 0.8, a 1.0, a 1.5, a 1.8, a 2.0, a 4.0, a 8.0 cm (inside diameter) pipe and the extruded articles are allowed to cool to room temperature. Light from a Spectra Physics Model 155A laser with a wavelength of about 632.80 nm is introduced at one end of each article and the light transmitted therethrough.

EXAMPLE XIX

Two plano-convex lenses of Example XVII are joined at their bases to form a sphere. The resultant sphere is thrown against a hard smooth glass door and upon impact is deformed into the shape of a pancake; upon recovery back to the original shape of a sphere, it slowly roll down the surface of the door under the force of gravity. The lenses are then joined at their base with only half of the total base surface areas overlapping; the joined lenses are thrown against a hard smooth glass door and upon recovery the lenses in union rolls down the surface of the door showing cam rolling action.

EXAMPLE XX

The lenses of Example XVII are deformed by two thin, rigid optical surface conforming sandwich sheets. The resulting deformed gelatinous lenses are used to view news print and other objects.

EXAMPLE XXI

The composition of EXAMPLE II is formed into wheels for a motorized and a free rolling vehicle capable of ascending or descending on a substantially glass, metal, and gloss painted inclined surface (greater than about 45 degree angle). It is contemplated that the non-adhesive tack nature of the composition may be useful as wheels or traction material for a vehicle capable of roving on the internal or external surfaces of a space ship or a space station under zero gravity conditions.

EXAMPLE XXII

Example II is repeated except about 980 parts oil containing 100 parts of a $Fe_3O_4$ magnetic particle is used and the gel rigidity is found to be within the range of about 20 to 700 gram Bloom.

EXAMPLE XXIII

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XXIV

The wheels of Example XXI is formed by casting the composition over a wheel shaped open cell sponge surface to form wheels having reduced weight.

EXAMPLE XXV

The composition of Example XXI is casted unto the surface of a Duocel open cell metal sponge.

EXAMPLE XXVI

The composition of Example XXI is casted unto a SCOTFOAM ® ⅛" thick: 5, 10, 15, 20, 25, 30, 35, 40, 45, 50, 60, 70, 80, 90, 100, and 200 ppi foam sheet.

EXAMPLE XXVII 2 inch lengths of 2, 4, 8, 10, and 20 mm diameter Polyester fibers are laid parallel (10 to 20 fibers per radial inch) to each other forming a radial array with an inner radial open space of about 1.5 inches, composition in the form of a 2.0 inch diameter lens is casted (positioned) centered on the polyester fiber array. Upon cooling, the fibers encapsulated by the composition at the equator "rim" can be stretched radially to focus the lens body (adjust the contour of the lens).

EXAMPLE XXVIII

The procedure of Example II is repeated except Shell Kraton G 1855X, poly(styrene-ethylene-butylene-styrene) triblock copolymer is used having a styrene end block to ethylene and butylene center block ratio of about 27:73 and the gel rigidity is found to be within the range of about 10 to about 800 gram Bloom.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. A gelatinous elastomer composition consisting essentially of:
   (a) 100 parts by weight of a high viscosity triblock copolymer of the general configuration poly(styrene-ethylene-butylene-styrene);
   (b) from about 300 to about 1,600 parts by weight of a plasticizing oil; said composition characterized by a gel rigidity of from about 20 to about 700 gram Bloom.

2. A gelatinous elastomer composition consisting essentially of:
   (a) 100 parts by weight of a high viscosity triblock copolymer of the general configuration poly(styrene-ethylene-butylene-styrene); said styrene to ethylene and butylene is of a ratio of from about 20:80 to about 40:60; and
   (b) from about 300 to about 1,600 parts by weight of a plasticizing oil; said composition characterized by a gel rigidity of from about 20 to about 700 gram Bloom.

3. A gelatinous elastomer composition consisting essentially of:
   (a) 100 parts by weight of a high viscosity triblock copolymer of the general configuration poly(styrene-ethylene-butylene-styrene); said styrene to ethylene and butylene is of a ratio of from about 30:70 to about 40:60; and
   (b) from about 300 to about 1,600 parts by weight of a plasticizing oil; said composition characterized by a gel rigidity of from about 20 to about 700 gram Bloom.

4. A gelantinous elastomer composition consisting essentially of:
   (a) 100 parts by weight of a high viscosity triblock copolymer of the general configuration poly(styrene-ethylene-butylene-styrene); said styrene to ethylene and butylene is of a ratio of from about 31:69 to about 40:60; and
   (b) from about 300 to about 1,600 parts by weight of a plasticizing oil; said composition characterized by a gel rigidity of from about 20 to about 700 gram Bloom.

5. A gelatinous elastomer composition of claim 1, 2, 3 or 4 wherein said triblock copolymer is characterized by a Brookfield Viscosity of a 20 weight percent solids solution in toluene at 25° C. of at least about 1,800 cps.

6. A gelatinous elastomer composition of claim 1, 2, 3 or 4 wherein said composition is casted with an open cell foam, said triblock copolymer is characterized by a Brookfield Viscosity of a 20 weight percent solids solution in toluene at 25° C. of at least about 1,800 cps.

* * * * *